United States Patent [19]

March

[11] 4,014,321
[45] Mar. 29, 1977

[54] NON-INVASIVE GLUCOSE SENSOR SYSTEM

[76] Inventor: Wayne F. March, 2517 Rugby Road, Dayton, Ohio 45406

[22] Filed: Oct. 6, 1975

[21] Appl. No.: 619,954

Related U.S. Application Data

[63] Continuation-in-part of Ser. No. 526,581, Nov. 25, 1974, Pat. No. 3,958,560.

[52] U.S. Cl. .............................. 128/2 A; 128/2 L; 128/2 T; 356/39
[51] Int. Cl.² .......................................... A61B 5/00
[58] Field of Search ........... 128/2 A, 2 L, 2 T, 2 E, 128/2.1 E; 351/9; 356/39–41, 51

[56] References Cited

UNITED STATES PATENTS

| | | | |
|---|---|---|---|
| 3,412,729 | 11/1968 | Smith, Jr. | 128/2 L |
| 3,512,517 | 5/1970 | Kadish et al. | 128/2 E |
| 3,638,640 | 2/1972 | Shaw | 128/2 L |
| 3,648,685 | 3/1972 | Hepp et al. | 128/2 L |
| 3,769,961 | 11/1973 | Fatt et al. | 128/2 T |
| 3,963,019 | 6/1976 | Quandt | 128/2 T |

OTHER PUBLICATIONS

Nature, vol. 214, June 3, 1967, pp. 986–988.
California Medicine, June, 1963, vol. 98, No. 6, pp. 325–327.
Diabetes, vol. 21, Suppl. 2, 1972, pp. 703–712.

Primary Examiner—Kyle L. Howell
Attorney, Agent, or Firm—Alter and Weiss

[57] ABSTRACT

A unique glucose sensor to determine the glucose level in patients, for example, for use in treating or diagnosing diabetes. The patient's eye is automatically scanned using a dual source of polarized radiation, each transmitting at a different wavelength at one side of the cornea of the patient. A sensor located at the other side of the cornea detects the optical rotation of the radiation that passed through the cornea. The level of glucose in the bloodstream of the patient is a function of the amount of the optical rotation of the radiation detected at the other side of the cornea of the patient. The result is transmitted to a remote receiver that is coupled to a readout device to thereby provide non-invasive glucose determinations of high specificity and reliability.

15 Claims, 5 Drawing Figures

NON-INVASIVE GLUCOSE SENSOR SYSTEM

This invention relates to diagnostic and/or curative instruments utilized by modern medicine and more particularly, to non-invasive automatic glucose sensing systems, and is a continuation in part of my patent application entitled NON-INVASIVE AUTOMATIC GLUCOSE SENSORY SYSTEM, filed on Nov. 25, 1974 and bearing Serial No. 526,581 which issued as U.S. Pat. No. 3,958,560, on May 25, 1976.

At the present, to determine the amount of glucose in the patients system for thereby determining whether or not the patient has diabetes or has need of insulin, urine or blood specimens are examined. It is well known that the glucose level varies in people. It is especially important to know what the glucose level is in people afflicted with diabetes. In the diabetics the level often reaches the point where it is necessary to provide the patient with insulin.

The present method of detecting and treating diabetic patients is for the patient to provide the hospital, doctor or lab technician with the specimens of urine and/or blood which are analyzed. If diabetes is then found, insulin is prescribed. Since the glucose level in each individual is variable, the amount of insulin which the patient takes does not necessarily correlate to the average glucose level. Nonetheless, there is no present method of reliably indicating to the patient that it is necessary for him to take insulin at a certain time or for readily determining the glucose level in the patient's blood. Thus, many patients do not take the necessary insulin when they really need it with the consequent adverse effects. Alternatively, many patients take more insulin than they need and suffer from hypoglycemia.

Thus, the present systems are inadequate because, among other things, they only give instantaneous readings. Further, the blood sample method requires puncturing the skin with a hypodermic device which is inconvenient, time consuming and bothersome. Further, as pointed out, the blood sugar varies widely with variables in the daily routine, such as acute illness, diet, physical exercise, etc. This means, that the routine insulin dose may be totally incorrect for a day that is not routine.

Accordingly, an object of the present invention is to provide convenient methods and equipment for continuously monitoring the control of glucose level in diabetics.

A further object of the present invention is to provide sensitive, non-invasive glucose sensor means which can diagnose new cases of diabetes.

Yet another object of the present invention is to provide glucose sensing devices that give automatic readouts showing how much glucose is present so that a person with a minimum of training, such as the patient himself, or a simple computer can reliably determine the diabetic control, and therefore, know whether or not to administer insulin.

Still another object of the present invention is to provide glucose sensing devices of previously unheard of specificity.

In accordance with a preferred embodiment of the invention a variation of saccharimetry is used to determine the presence and level of glucose in the patient's blood. A contact lens shaped to fit over the cornea is provided with built-in collimated radiation sources, such as dual laser transmitters on one side thereof and a detector on the other side. The laser beams are transmitted through a first polaroid filter. A second polaroid filter rotated with respect to the first filter is provided in front of the detector A power source is also mounted in the contact lens. The laser transmitters are aimed to cause the radiation to pass through the cornea and the aqueous humor to the detector. A telemetry transmitter is mounted adjacent to the detector and coupled thereto for transmitting a signal that is a function of the optical rotation of the laser beam caused by the glucose. A remote receiver functions to receive the signal transmitted and couples that signal to a readout device which automatically provides a readout determinative of the glucose content in the aqueous humor which is directly proportional to the glucose content of the blood.

These and other projects and features of the invention will be now explained with the aid of the accompanying drawings, in which.

Figure 1:
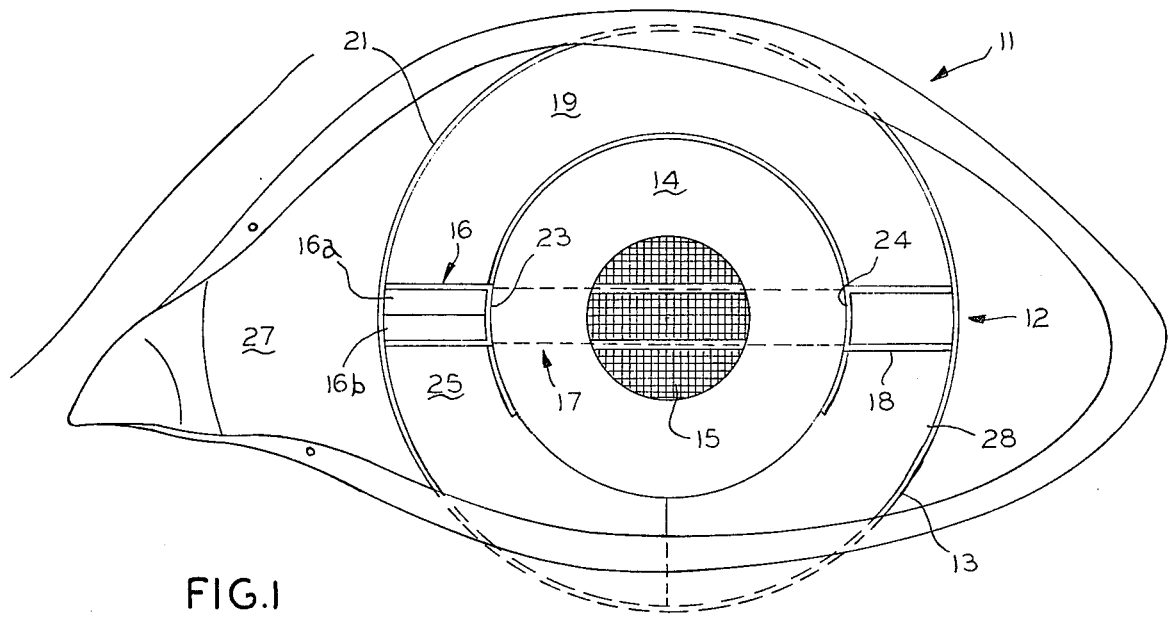
FIG. 1 is a front view of the patient's eyeball having a contact lens thereon which is equipped with the glucose sensor system.
Figure 2:
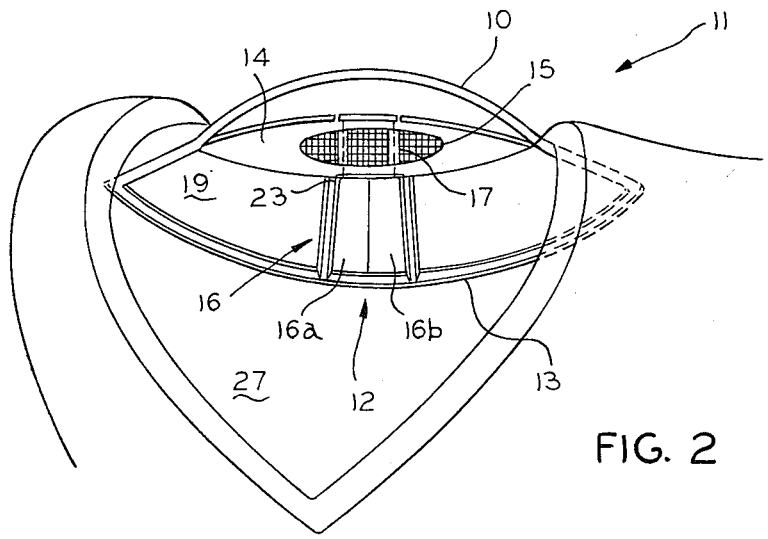
FIG. 2 is a side view of the eyeball of FIG. 1 having the lens thereon with the non-invasive glucose sensor system mounted thereto.

As shown in FIGS. 1 and 2, the eye, generally shown as 11, is equipped with a non-invasive glucose sensor system, generally shown as 12. The glucose sensor system is mounted into a contact lens 13. The contact lens is preferably a soft scleral contact lens which permits visible light to pass but no infrared. The lens fits over the cornea and part of the scleral 27, covering the iris 14.

As can be seen, particularly, in FIG. 2, the cornea 10 covering the iris 14 and the pupil 15 resembles a mound in that it has a different radius of curvature; and therefore, rises above the level of the rest of the eyeball. The non-invasive glucose sensor system is shown mounted at the periphery of the iris. Radiation source means are provided. For example, a radiation source 16 including radiation transmitters 16a and 16b are shown mounted in the contact lens at one side of the iris fitted with a polarizing filter 23. The sources shown emit infrared radiation shown at 17, which passes through a second polarizing filter 24 and is received by the infrared radiation detector 18. The amount of radiation receive by the infrared radiation detector 18 is a function of the glucose in the patient's blood.

Also, shown is a power source 19 mounted in the contact lens which may be any well known small nickel cadmium battery; for example, coupled to the source 16 and to detector 18 to provide it with the necessary power.

One preferrable source of infrared radiation is a gallium arsenide indium laser. Two lasers may be used to generate infrared radiation at two wavelengths, such as 0.98 and 0.78 micron. An advantage of using two laser beams of different wavelengths is that telemetering the ratio of radiation detected at the two wavelengths increases the specificity of the equipment thereby precluding errors due to other substances, such as lactate, in the aqueous. Each substance causes its own characteristic optical activity at each different wavelength.

The polarizing filters in a preferred embodiment of the invention are Glan-Thompson type prisms. The emitters used are models FIP 325 circuits and the silicon detector used to a type DDV 325 circuit as provided by Meret, Inc. of Santa Monica, California. It should be understood that other radiation emitting, filtering, and detecting means are within the scope of the invention.

The detector 18 is shown at the other side of the iris mounted in the contact lens. When the laser beams pass through the aqueous humor, they are optically rotated as a function of the glucose therein. Therefore, the infrared radiation that is received is a function of the sugar content. The rotation occurs because the hydroxyl in glucose absorbs the polarized infrared beam in an optically active manner, thereby rotating the beam.

Figure 3:
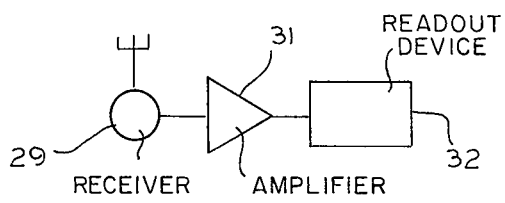
FIG. 3 is a block diagram showing of a receiving system providing a readout of the glucose content as determined by the non-invasive sensor system.

Means are provided for transmitting the detected output. More particularly, a transmitter 28 sends the detected signal through antenna 21. The detected signal is received at a receiver, such as receiver 29. As schematically shown in FIG. 3 the signal from the receiver is amplified at amplifier 31 which is connected to a logic and readout device 32.

Figure 4:
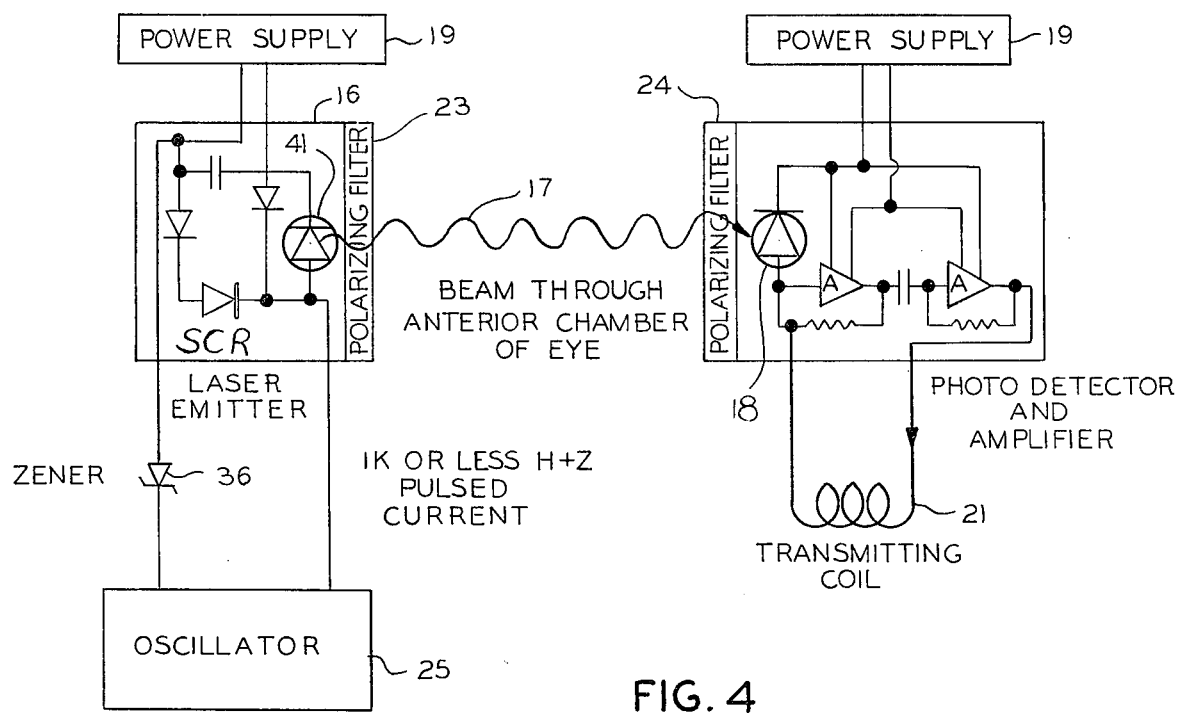
FIG. 4 is a simplified schematic of the glucose sensor system.

As shown in FIG. 4 an oscillator circuit 25 is embedded within the contact lens for the purpose of pulsing the laser circuits.

One preferred embodiment utilized a 50 nanosecond pulse every millisecond. This relatively large pulsewith and frequency band can effectively be powered by batteries requiring only 300 milliwatts to produce 6 watts of radiation. The pulse rates are the same for both lasers, but the pulses are made to occur at different points of the cycle to avoid any confusion.

Amplifying circuits within the transmitter 28 amplify the detected signal prior to the transmission through coil 21. It should be understood that a simple transmitting circuit is shown. However, more complicated systems using modulation are within the scope of the invention.

The circuit of a suitable phaselock telemetry receiver, such as schematically shown in FIG. 3 is described in a book entitled BIOMEDICAL TELEMETRY by R. S. Mackay published by John Wiley & Sons, Inc. in 1970. The logic device 29 may be model 756 circuit available from Analog Devices, Inc. in Norwood, Massachusetts. The logic device is used to determine the concentration of glucose from the telemetry signals. The device solves the following equation, whose derivation is shown as follows:

$$c = \frac{\ln[2I_1 + 2\sqrt{I_1(I_1-1)} - 1]}{0.11} - \frac{\ln[2I_2 + 2\sqrt{I_2(I_2-1)} - 1]}{0.11}$$

wherein:
- $c$ = Concentration of glucose in %
- $\alpha_1$ = Optical rotation in degrees at 0.98 micron
- $\alpha_2$ = Optical rotation in degrees at 0.78 micron
- $k$ = Proportionality constant
- $I_1$ = Amplitude of telemetry signal resulting from laser operating at a wavelength of 0.98 micron
- $I_2$ = Amplitude of telemetry signal resulting from laser operating at a wavelength of 0.78 micron

| STEP | EQUATION | DERIVATION |
|---|---|---|
| A | $\cos^2\alpha = I$ | From Polarized Light W. A. Shurcliff and S. S. Ballard, Van Nostrand Co., p. 67, 1964. |
| B | $\cos\alpha = \frac{e^{i\alpha} + e^{-i\alpha}}{2}$ | Identity |
| C | $\cos^2\alpha = \frac{e^{2i\alpha} + e^{-2i\alpha}}{4} + \frac{1}{2}$ | |
| | $\frac{e^{2i\alpha} + e^{-2i\alpha}}{4} + \frac{1}{2} = I$ | From A and C |
| | $e^{2i\alpha} = 2I + 2\sqrt{I(I-1)} - 1$ | |
| D | $\alpha = \frac{\ln[2I + 2\sqrt{I(I-1)} - 1]}{2i}$ | | but
$Ekc = \alpha$
and
$Fk_1c = \alpha_1$
$Gk_2c = \alpha_2$ $k_1c - k_2c = \alpha_1 - \alpha_2$ ... Substracting G from F $k_1 = 0.090, k_2 = 0.035$ ... Experimentally determined H $\quad c = \frac{\alpha_1 - \alpha_2}{0.055}$ $$c = \frac{\frac{\ln[2I_1 + 2\sqrt{I_1(I_1-1)} - 1]}{2i} - \frac{\ln[2I_2 + 2\sqrt{I_2(I_2-1)} - 1]}{2i}}{0.055}$$

Substituting for $\alpha$ from step D.

In FIG. 4 the oscillator 25 is shown connected to the power supply 19 through zener regulator 36. The pulse signals are connected to the laser emitting circuits 16. The laser beam 17 passes through the polarizing filter 23 of the emitter unit 16 and to the polarizing unit 24 of the detector 18.

Figure 5:
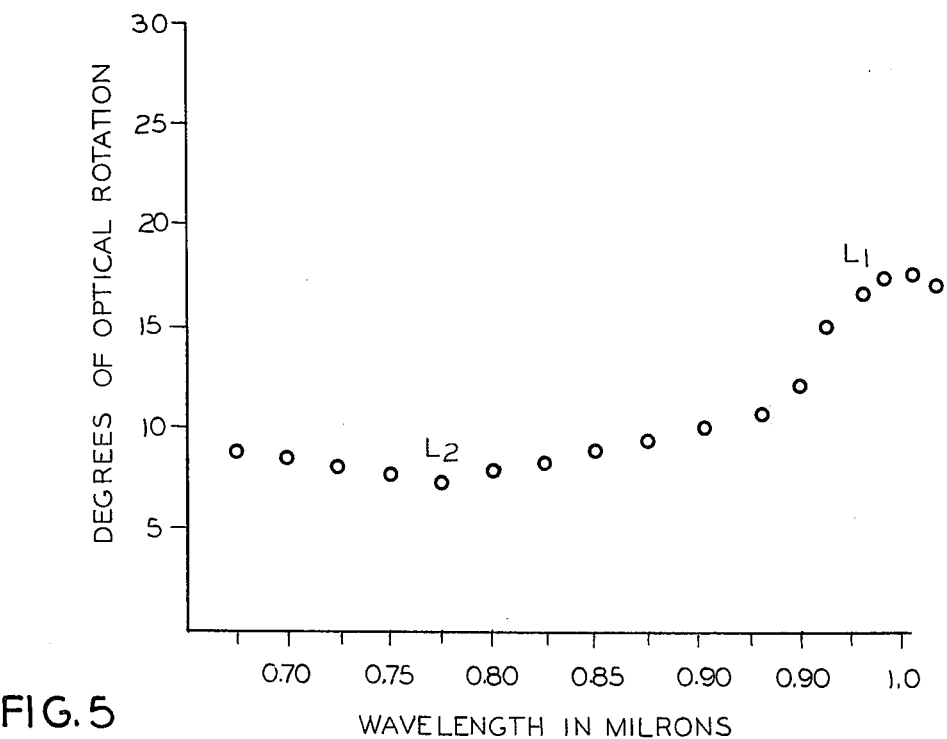
FIG. 5 is a graph illustrating the optical rotary dispersion of a 10% glucose solution to aid in understanding the invention.

In a preferred embodiment of the invention, one of the lasers operates at 0.98 microns as indicated by L1 on the graph of FIG. 5. The other laser operates at 0.78 microns as indicated by L2 on the graph.

The graph was derived by experimentation using a 10% glucose solution. This compares to a normal glucose concentration in the aqueous humor of 0.1%. It should be noted that it has been found that at 0.98 micron the optical rotation caused by other substances in the aqueous humor, such as lactate, is practically negligible. The optical rotation caused in the experimental glucose solution at 0.98 micron was found to be 18° (See FIG. 5). The optical rotation at 0.78 micron was found to be approximately 7°. The radiation in the experiment went through a tube 2 decimeters in length. Since this tube is approximately 20 times the lenth of the cornea, a factor of one-twentieth must be incorporated in the constant. Then the equation solved by the logic block of FIG. 3 gives the concentration of the glucose in the aqueous humor.

Means are provided for screening out extraneous infrared radiation. More particularly, the contact lens preferrably has different additives mixed in the plastic during the manufacturing of the lens. This produces a lens material that is opaque to infrared, but possesses only a slight blue tint. The components of the non-invasive glucose system are placed in the plastic as it is cured.

The collimated polarized radiation is transmitted through the glucose containing aqueous and is rotated, varying the amount of radiation passing through the receiving prism to the detector. Signals indicating the amount of light are transmitted through a receiver to a logic circuit which is set to solve an equation providing an instantaneous readout of the concentration of the glucose in the aqueous.

Thus, the non-invasive method and equipment described herein in operation detects the glucose concentration instantaneously in the aqueous humor of the eye in vivo by measuring the optical rotation at two wavelengths of polarized light detected through the anterior chamber of the eye.

While the principles of the invention have been described above in connection with specific apparatus and applications, it is to be understood that this description is made by way of example, and not as a limitation on the scope of the invention.

I claim:

1. A non-invasive glucose sensor system for determining the sugar content in a user's blood,
said system comprising radiation emitting means for emitting radiation of certain wavelengths,
radiation detecting means for detecting the emitted radiation,
said radiation detecting means spaced apart from but in line with said radiation emitting means,
means for mounting said radiation emitting means and radiation detecting means so that said radiation is capable of being transmitted through the cornea of the user's eye, and
enabling means for enabling said detecting means to determine the optical rotation of the radiation occurring in the cornea.

2. The non-invasive glucose sensor system of claim 1 wherein said enabling means comprises an optical polarizing system,
said optical polarizing system including first polarizing means for polarizing said emitted radiation prior to the transmission thereof through the cornea, and
second polarizing means mounted on the detector side of said cornea and rotated with respect to said first polarizing means.

3. The non-invasive glucose sensor system of claim 1 wherein said radiation emitting means comprises a pair of laser emitters operating at different wavelengths.

4. The non-invasive glucose sensor system of claim 1 wherein said means for mounting said radiation emitting means and said radiation detecting means comprises contact lens means.

5. The non-invasive glucose sensor system of claim 4 wherein said contact lens means are opaque to infrared radiation and wherein the radiation traveling from said radiation emitting means to said radiation detecting means does not pass through said contact lens means.

6. The non-invasive glucose sensor system of claim 5 wherein said contact lens means is a soft scleral contact lens.

7. The non-invasive glucose sensor system of claim 1 wherein means are provided for transmitting a signal that is a function of the detected radiation obtained from said radiation detector means and receiving means for receiving said transmitted signal to provide an indication of the glucose content of the user's blood.

8. The non-invasive glucose sensor system of claim 7 wherein said receiving means includes logic means for providing the solution to the following equation:

$$c = \frac{\ln[2I_1 + 2\sqrt{I_1(I_1-1)} - 1]}{0.11} - \frac{\ln[2I_2 + 2\sqrt{I_2(I_2-1)} - 1]}{0.11}$$

wherein:
$c$ = Concentration of glucose in %
$\alpha_1$ = Optical rotation in degrees at 0.98 micron
$\alpha_2$ = Optical rotation in degrees at 0.78 micron
$k$ = Proportionality constant
$I_1$ = Amplitude of telemetry signal resulting from laser operating at a wavelength of 0.98 micron
$I_2$ = Amplitude of telemetry signal resulting from laser operating at a wavelength of 0.78 micron

| STEP | EQUATION | DERIVATION |
|---|---|---|
| A | $\cos^2\alpha = I$ | From Polarized Light W. A. Shurcliff and S. S. Ballard, Van Nostrand Co., p. 67, 1964. |
| B | $\cos\alpha = \frac{e^{i\alpha} + e^{-i\alpha}}{2}$ | Identity |
| C | $\cos^2\alpha = \frac{e^{2i\alpha} + e^{-2i\alpha}}{4} + \frac{1}{2}$ | |
| | $\frac{e^{2i\alpha} + e^{-2i\alpha}}{4} + \frac{1}{2} = I$ | From A and C |
| | $e^{2i\alpha} = 2I + 2\sqrt{I(I-1)} - 1$ | |
| D | $\alpha = \frac{\ln[2I + 2\sqrt{I(I-1)} - 1]}{2i}$ | | but
$Ekc = \alpha$
and
$Fk_1c = \alpha_1$
$Gk_2c = \alpha_2$ $k_1c - k_2c = \alpha_1 - \alpha_2$ ... Subtracting G from F $k_1 = 0.90, k_2 = 0.035\ldots$ Experimentally determined H  $\quad c = \dfrac{\alpha_1 - \alpha_2}{0.055}$ $$c = \dfrac{\dfrac{\ln[2I_1 + 2\sqrt{I_1(I_1-1)} - 1]}{2i} - \dfrac{\ln[2I_2 + 2\sqrt{I_2(I_2-1)} - 1]}{2i}}{0.055}$$

Substituting for $\alpha$ from step D.

9. A method of obtaining the sugar content of a person non-invasively,
said method comprising the steps of:
generating a pair of radiation rays and polarizing said pair of radiation rays;
transmitting said polarized radiation rays through the cornea of a patient's eye;
filtering said polarized radiation rays received from said cornea through a polarized filter; and
detecting the filtered polarized radiation rays which have been passed through the cornea of the patient's eyes; and
translating the detected radiation rays to obtain a readout indicative of the sugar content of the patient's blood.

10. The method of claim 9 wherein said pair of radiation rays comprises a first radiation ray having a wavelength of 0.98 micron and a second radiation ray having a wavelength of 0.78 micron.

11. The method of claim 9 including the step of blocking out extraneous infrared radiation.

12. The method of claim 9 wherein said radiation rays are transmitted for 50 nanoseconds every millisecond.

13. The method of claim 12 including the step of: mounting said radiation generating and transmitting means and optical rotation detecting means as well as transmitter means onto a contact lens and placing the contact lens in the patient's eye.

14. The method of claim 9 including the steps of:
transmitting a signal that is a function of the detected radiation;
receiving the signal that is a function of the detected signal; and
translating the received signal into a digital readout indicative of the sugar content of the person's blood.

15. The method of claim 14 wherein said translating comprises solving the equation:

$$c = \dfrac{\ln[2I_1 + 2\sqrt{I_1(I_1-1)} - 1]}{0.11} - \dfrac{\ln[2I_2 + 2\sqrt{I_2(I_2-1)} - 1]}{0.11}$$

wherein:
$c$ = Concentration of glucose in %
$\alpha_1$ = Optical rotation in degrees at 0.98 micron
$\alpha_2$ = Optical rotation in degrees at 0.78 micron
$k$ = Proportionality constant
$I_1$ = Amplitude of telemetry signal resulting from laser operating at a wavelength of 0.98 micron
$I_2$ = Amplitude of telemetry signal resulting from laser operating at a wavelength of 0.78 micron

| STEP | EQUATION | DERIVATION |
|---|---|---|
| A | $\cos^2\alpha = I$ | From Polarized Light W. A. Shurcliff and S. S. Ballard, Von Nostrand Co., p. 67, |
| B | $\cos\alpha = \dfrac{e^{i\alpha} + e^{-i\alpha}}{2}$ | Identity |
| C | $\cos^2\alpha = \dfrac{1}{2}\cdot\dfrac{e^{2i\alpha} + e^{-2i\alpha}}{4} + \dfrac{1}{2}$ | |
| | $\dfrac{e^{2i\alpha} + e^{-2i\alpha}}{4} + \dfrac{1}{2} = I$ | From A & C |
| | $e^{2i\alpha} = 2I + 2\sqrt{I(I-1)} - 1$ | |
| D | $= \dfrac{\ln[2I + 2\sqrt{I(I-1)} - 1]}{2i}$ | |
| but E and F G | $kc = \alpha$ $k_1 c = \alpha_1$ $k_2 c = \alpha_2$ $k_1 c - k_2 c = \alpha_1 - \alpha_2$ $k_1 = 0.90, k_2 = 0.035$ | Subtracting G from F Experimentally determined |
| H | $c = \dfrac{\alpha_1 - \alpha_2}{0.055}$ | |
| | $c = \dfrac{\dfrac{\ln[2I_1 + 2\sqrt{I_1(I_1-1)} - 1]}{2i} - \dfrac{\ln[2I_2 + 2\sqrt{I_2(I_2-1)} - 1]}{2i}}{0.055}$ | Substituting for $\alpha$ from step D. |

\* \* \* \* \*